(12) United States Patent
Ossetrova

(10) Patent No.: US 9,063,148 B2
(45) Date of Patent: Jun. 23, 2015

(54) IMMUNOASSAYS FOR CITRULLINATED PROTEINS

(75) Inventor: Natalia Ossetrova, Silver Spring, MD (US)

(73) Assignee: THE HENRY M. JACKSON FOUNDATION FOR THE ADVANCEMENT OF MILITARY MEDICINCE, INC., Bethesda, MD (US)

( * ) Notice: Subject to any disclaimer, the term of this patent is extended or adjusted under 35 U.S.C. 154(b) by 150 days.

(21) Appl. No.: 13/125,018

(22) PCT Filed: Oct. 22, 2009

(86) PCT No.: PCT/US2009/061660
§ 371 (c)(1),
(2), (4) Date: Jun. 9, 2011

(87) PCT Pub. No.: WO2010/048388
PCT Pub. Date: Apr. 29, 2010

(65) Prior Publication Data
US 2011/0244492 A1 Oct. 6, 2011

Related U.S. Application Data

(60) Provisional application No. 61/107,446, filed on Oct. 22, 2008.

(51) Int. Cl.
*G01N 33/00* (2006.01)
*G01N 33/68* (2006.01)

(52) U.S. Cl.
CPC ........ *G01N 33/6812* (2013.01); *G01N 33/6893* (2013.01); *G01N 2800/40* (2013.01)

(58) Field of Classification Search
None
See application file for complete search history.

(56) References Cited

U.S. PATENT DOCUMENTS

| | | | | |
|---|---|---|---|---|
| 5,420,016 | A * | 5/1995 | Boguslaski et al. | 435/12 |
| 2007/0065886 | A1 * | 3/2007 | Bowen et al. | 435/7.4 |
| 2008/0026485 | A1 * | 1/2008 | Hueber et al. | 436/507 |
| 2009/0142792 | A1 * | 6/2009 | Robinson et al. | 435/29 |

OTHER PUBLICATIONS

Chang et al., Citrullination of fibronectin in rheumatoid arthritis synovial tissue, Rheumatology, Aug. 2005: 44: pp. 1374-1382.*
Ossetrova et al., The use of discriminant analysis for evaluation of early-response multiple biomarkers of radiation exposure using non-human primate 6-Gy whole-body radiation model, Radiation Measuremtns, vol. 42, Aug. 2007, pp. 1158-1163.*
Curis et al., Almost all about citrullline in mammals, Amino acids 2005, vol. 29, pp. 177-205.*
Lutgens et al., Plasma Citrulline concentration: A surrogate end point for radiation-induced mucosal atrophy of the small bowel, A feasibility study in 23 patients, Int. J. Radiation Oncology Biol. Phys., vol. 60, No. 1, pp. 275-285.*
Advanced Targeting Systems, Anti-conjugated Citrulline Rabbit Polyclonal, May 8, 2008, Specificity and Preparation.*
Utz et al., Death, autoantigen modifications and tolerance, Arthritis Res 2000, vol. 2: pp. 101-114.*
Waselenko et al., Medical Management of the Acute Radiaiton Syndrome: Recommendations of the Strategic National Stockpile Radiatin Working Group, Ann Intern Med. 2004;140: pp. 1037-1051.*
Soos et al., Clinical Evaluation of Anti-Mutated Citrullinated Vimentin by ELISA in Rheumatoid Arthritis, The Journal of Rheumatalogy, 2007; 34:8, pp. 1658-1663.*
AFRRI—Armed Forces Radiobiology Research Institute. Medical Management of Radiological Casualties. hnttp://www.afrri.usuhs.mil/www/outreach/mmoresources.htm, 2003 (166 pages).
Arai T, Kusubata M, Kohsaka T, Shiraiwa M, Sugawara K, Takahara H. 1995. Mouse uterus peptidylarginine deiminase is expressed in decidual cells during pregnancy. J Cell Biochem 58(3): 269-278.
Bendahan D, Mattei J P, Ghattas B, Confort-Gouny S, Le Guern M E, Cozzone P J. 2002. Citrulline/malate promotes aerobic energy production in human exercising muscle. British Journal of Sports Medicine 36(4):282-289.
Blijlevens N M, Lutgens L C, Schattenberg A V, Donnelly JP. 2004. Citrulline: a potentially simple quantitative marker of intestinal epithelial damage following myeloablative therapy. Bone Marrow Transplant. 34(3):193-6.
Buell M G, Harding R K. 1989. Proinflammatory effects of local abdominal irradiation on rat gastrointestinal tract. Dig Dis Sci 34(3): 390-399.
Callis A, Magnan de Bornier B, Serrano J, Serrano J J, Bellet H, Saumade R. 1991. Activity of Citrruline malate on acid-base balance and blood ammonia and amino acid levels. Arzneimittel-Forschung/Drug Research, 41(6): 660-663.
Cameron J L, Koerker D J, and Steiner R A. 1985. Metabolic changes during maturation of male monkeys: possible signals for onset of puberty. Am J Physiol Endocrinol Metab 249:E385-E391.
Chao W R, Berridge B J Jr, Peters J H. 1973. Amino acid levels in the plasma of fasting macaques (*Macaca cyclopis*, *M. fascicularis*, and *M. mulatta*). Laboratory Animal Science, 23(3):380-384.

(Continued)

*Primary Examiner* — Gary W Counts
(74) *Attorney, Agent, or Firm* — Foley & Lardner LLP

(57) ABSTRACT

Methods and kits are provided for assessing radiation injury and exposure in a mammal. The methods comprise the steps of: obtaining one or more test samples from the mammal, contacting the test samples with an antibody immunoreactive with a citrullinated protein to form an immunocomplex; and detecting the immunocomplex with an ELISA; wherein a decrease in the quantity of the immunocomplex in the test samples, as compared to the quantity of immunocomplexes formed under identical conditions with the same antibody and a control sample from one or more mammals known to have a lower degree of radiation injury or exposure, indicates a higher degree of radiation injury and exposure to the mammal. The information obtained from such methods can be used by a clinician to accurately assess the extent of radiation injury/exposure in the mammal, and thus will provide a valuable tool for determining treatment protocols on a subject by subject basis.

9 Claims, 12 Drawing Sheets

(56) References Cited

OTHER PUBLICATIONS

Demina M V, Zemtsova N A, Muromtseva G A. 1999. Treating Fatigue Syndrome in Chernobyl Nuclear Power Plant Disaster Liquidators with Neurocirculatory Dystonia. Healing Physician 1:56-57. 6 pages.
Dixon B. 1985. The biological and clinical effects of acute whole or partial body irradiation. J. Soc. Radiol. Prot. 5(3): 121-128.
Giannesini B, Izquierdo M, Le Fur Y, Cozzone P J, Verleye M, Le Guern M E, Gillardin J M, Bendahan D. 2009. Beneficial effects of citrulline malate on skeletal muscle function in endotoxemic rat. European Journal of Pharmacology 602(1): 143-147.
Gillett N A, Muggenburg B A, Boecker B B, et al. 1987. Single inhalation exposure to 90SrCl2 in the beagle dog: Hematological effects. Radiation Research 110: 267-288.
Hagiwara T, Nakashima K, Hirano H, Senshu T, Yamada M. 2002. Deimination of arginine residues in nucleophosmin/B23 and histones in HL-60 granulocytes. Biochem Biophys Res Commun 290(3): 979-983.
Hahn F F, Barnes J E, Hobbs C H, and Mauderly J L. 1975. Effect of $^{90}$Y Inhaled in fused clay particles on the gastrointestinal tract of Beagles. Radiation Research 61: 444-456.
Hill J, Cairns E, Bell D A. 2004. The joy of citrulline: new insights into the diagnosis, pathogenesis, and treatment of rheumatoid arthritis. J Rheumatol 31(8): 1471-1473.
Ishigami, A., Ohsawab, T., Asagab, H., Akiyama, K., Kuramotoa, M., Maruyamaa, N. 2002. Human peptidylarginine deiminase type II: molecular cloning, gene organization, and expression in human skin. Archives of Biochemistry and Biophysics 407(1): 25-31.
Ishiyama N, Bates I R, Hill C M, Wood D D, Matharu P, Viner N J, Moscarello M A, Harauz G. 2001. The effects of deimination of myelin basic protein on structures formed by its interaction with phosphoinositide-containing lipid monolayers. J Struct Biol 136(1):30-45.
Kanno T, Kawada A, Yamanouchi J, Yosida-Noro C, Yoshiki A, Shiraiwa M, Kusakabe M, Manabe M, Tezuka T, Takahara H. 2000. Human peptidylarginine deiminase type III: molecular cloning and nucleotide sequence of the cDNA, properties of the recombinant enzyme, and immunohistochemical localization in human skin. J Invest Dermatol 115(5): 813-823.
Lutgens L C, Blijlevens N M, Deutz N E, Donnelly J P, Lambin P, de Pauw B E. 2005. Monitoring myeloablative therapy-induced small bowel toxicity by serum citrulline concentration: a comparison with sugar permeability tests. Cancer 103(1): 191-199.
Lutgens L C, Deutz N E, Gueulette J, Cleutjens J P, Berger M P, Wouters B G, von Meyenfeldt M F, Lambin P. 2003. Citrulline: a physiologic marker enabling quantitation and monitoring of epithelial radiation-induced small bowel damage. Int J Radiat Oncol Biol Phys. 57(4):1067-1074.
Lutgens L, Lambin P. 2007. Biomarkers for radiation-induced small bowel epithelial damage: an emerging role for plasma Citrulline. World J Gastroenterol. 13(22): 3033-3042.
Nakashima K, Hagiwara T, Ishigami A, Nagata S, Asaga H, Kuramoto M, Senshu T, Yamada M. 1999. Molecular characterization of peptidylarginine deiminase in HL-60 cells induced by retinoic acid and 1alpha,25-dihydroxyvitamin D(3). J Biol Chem 274(39): 27786-27792.
Peters J H, Berridge B J Jr, Chao W R, Cummings J G, Lin S C. 1971 Amino acid patterns in the plasma of old and new world primates. Comparative biochemistry and physiology, 39(3):639-647.
Peters J H, Smith C C. Amino acids and L-asparaginase activity in the plasma of owl monkeys (*Aotus trivirgatus*). 1972. Journal of medical primatology 1(5): 326-332.
Peters J H, Tanaka T. 1972. Amino Acids in the Plasma of Fasting Japanese Monkeys (*Macaca fuscata fuscata* and *M. f. yakui*). Primates 13(3): 271-276.
Rogers G, Winter B, McLaughlan C, Powell B, Nesci T. 1997. Peptidylarginine deiminase of the hair follicle: characterization, localization, and function in keratinizing tissues. J Invest Dermatol 108(5): 700-707.
Rogers, G. E. 1962. Occurrence of citrulline in proteins. Nature 194: 1149-1151.
Stegink L D, et al., 1981. Placental transfer of taurine in the rhesus monkey. The American Journal of Clinical Nutrition 34: 2685-2692.
Stone, H. B., et al., 2004. Models for evaluating agents intended for the prophylaxis, mitigation and treatment of radiation injuries. Report of an NCI Workshop, Dec. 3-4, 2003. Radiation Research 162(6): 711-728.
Vanuxem P, Vanuxem D, Formaris E, Bernasconi P. 1986. The role of lactate and ammonium in fatigue . Gazette Medicale 7: 67-68, 71-72.
Verleye M, Heulard I, Stephens J R, Levy R H, Gillardin J M. 1995. Effects of citrulline malate on bacterial lipopolysaccharide induced endotoxemia in rats. Arzneimittel-Forschung 45(6):712-715.
Wood D D and Moscarello M A. 1989. The isolation, characterization, and lipid-aggregating properties of a citrulline containing myelin basic protein. J Biol Chem 264(9): 5121-5127.
Tukachinsky, S.E. and Moiseeva, V.P., "Cx-Reactive Protein and the Radiation Syndrome," Biochem. Biophysics, (1960) 8:48-52 (6 pages).
Maltsev, V.N. et al., "Individual Prediction of the Gravity and Outcome of Acute Radiation Syndrome Based on Immunologic Indicators," Radiatsionnaya Biologiya, Radioekologiya, vol. 46(2): 152-158 (2006).
Maltsev, V.N. et al., "Blood Serum C-Reactive Protein as Indicator of the Gravity of Radiation Damage," Doklady Akedemii Nauk SSSR, vol. 239(3):750-752 (1978) (5 pages).
Crenn P et al., "Plasma citrulline: A marker of enterocyte mass in villous atrophy-associated small bowel disease," Gastroenterology. 124(5): 1210-19. (2003).
MacVittie, TJ et al., "Defining the full therapeutic potential of recombinant growth factors in the post radiation-accident environment: The effect of supportive care plus administration of G-CSF," Health Physics. 89(5): 546-555. (Nov. 2005).
Petrov, R. "Immunology of acute radiation injury," Joint Publications Research Service. Apr. 9, 1963. 305 pages. (pp. 185-212 are unavailable in original document; see footnote on p. 2).
Asaga et al., "Selective Deimination of Vimentin in Calcium Ionophore-Induced Apoptosis of Mouse Periotneal Macrophages," Biochemical and Biophysical Research Communications, vol. 243, pp. 641-646, 1998.
Tsuji et al., "Changing Pattern of Deiminated Proteins in Developing Human Epidermis," The Journal of Investigative Dermatology, vol. 120, No. 5, pp. 817-822, May 5, 2003.
Wood et al., "The Isolation, Characterization, and Lipid-aggregating Properties of a Citrulline Containing Myelin Basic Protein," The Journal of Biological Chemistry, vol. 264, No. 9, pp. 5121-5127, Mar. 25, 1989.
Tarcsa et al., "Protein Unfolding by Peptidylarginine Deiminase," The Journal of Biological Chemistry, vol. 271, No. 48, pp. 30709-30716, Nov. 29, 1996.
Vossenaar et al., "The Presence of Citrullinated Proteins is Not Specific for Rheumatoid Synovial Tissue," Arthritis and Rheumatism, vol. 50, No. 11, pp. 3485-3494, Nov. 2004.
Chapuy-Regaud et al., "Fibrin Deimination in Synovial Tissue is Not Specific for Rheumatoid Arthritis but Commonly Occurs during Synovitides," The Journal of Immunology, vol. 174, pp. 5057-5064, 2005.
Wang et al., "Human PAD4 Regulates Histone Arginine Methylation Levels via Demethylimination," Science, vol. 306, pp. 279-283, Oct. 8, 2004.
Cuthbert et al., "Histone Deimination Antagonizes Arginine Methylation," Cell, vol. 118, pp. 545-553, Sep. 3, 2004.

* cited by examiner

000# IMMUNOASSAYS FOR CITRULLINATED PROTEINS

CROSS REFERENCE TO PRIOR APPLICATIONS

This application is a U.S. national phase application under 35 U.S.C. §371 of International Patent Application No. PCT/US2009/061660 filed Oct. 22, 2009, which claims the benefit of U.S. Provisional Patent Application No. 61/107,446 filed Oct. 22, 2008, each of which is hereby incorporated by reference in its entirety.

STATEMENT REGARDING FEDERALLY SPONSORED RESEARCH

This invention was made in part with Government support under Award No. HU0001-05-D-0005 awarded by the Uniformed Services University of the Health Sciences. The Government may have certain rights in the invention.

FIELD OF THE INVENTION

This application relates generally to the rapid assessment of radiation injury and radiation exposure and, in particular, to the use of novel methods for determination of citrullinated proteins for assessing radiation injury and radiation exposure.

BACKGROUND OF THE INVENTION

Exposure to damaging ionizing radiation can stem from various sources and pose significant health risks. For example, military forces and inhabitants of metropolitan areas are at risk of exposure from a nuclear or radiological attack, industrial accidents, and environmental pollution. Patients are often subjected to ionizing radiation in the course of medical care, including X-ray diagnoses and therapies for cell-proliferative disorders.

Depending on the level of exposure, the effects of radiation can range from nausea and vomiting, to immune system compromise, and to death from radiation-induced tissue damage or infection. Exposure to moderate doses of gamma radiation has been shown to cause chromosomal damage and defects in hematopoiesis and immunosuppression. Successively higher radiation doses compound these effects with gastrointestinal (GI) and neurovascular tissue damage.

Ionizing radiation can trigger free-radical reactions that lead to the formation of reactive oxygen species (ROS). It is generally believed that production of ROS is a primary mechanism underlying radiation-induced biological damage. The cells of the immune and blood-forming systems are particularly sensitive to changes in oxidant/antioxidant balance due to the high percentage of polyunsaturated fatty acids in their plasma membranes. The oxidant/antioxidant balance is thus an important determinant for both immune and blood-forming functions, not only for maintaining the integrity and function of the plasma membrane, cellular proteins, and nucleic acids, but also for control of signal transduction and gene expression.

The triage of suspected radiation over-exposed individuals is critical to determine those individuals requiring appropriate medical treatment. Early treatment of populations exposed to ionizing radiation requires accurate and rapid biodosimetry to determine an individual's exposure level and risk for morbidity and mortality. Tissue specific protein biomarkers detected in peripheral blood can provide diagnostic information of organ specific radiation injury to the medical community to effectively manage radiation casualty incidents. The small bowel is a major dose-limiting organ with regard to both acute and late treatment-related morbidity when abdominal or pelvic cancers are treated with radiotherapy. Small bowel irradiation results in epithelial cell loss and consequently impairs function and metabolism. Amino acid citrulline, a metabolic end product of small bowel enterocytes, can be used for quantifying radiation-induced epithelial cell loss.

Currently available methods to measure citrulline level in blood plasma are high-performance liquid chromatography (HPLC) and gas chromatography/mass spectrometry (GC/MS). These methods require skilled personnel and expensive equipment, long time, and high cost to analyze samples and are not suited for repeated measurements as a routine in daily clinical practice.

The present invention provides assays for assessing radiation induced injury and exposure. The assays may be applicable in daily clinical practice during the acute and late phases of radiation injury, so that the most effective treatment can be provided to the subject. Furthermore, the information provided by the assays is sufficient to help a clinician develop the best possible means of treatment for each subject individually and depending on their level of exposure.

SUMMARY OF THE INVENTION

The invention provides methods for assessing radiation injury and exposure in a mammal, comprising the steps of: obtaining one or more test samples from the mammal, contacting the test samples with an antibody immunoreactive with a citrullinated protein to form an immunocomplex; and detecting the immunocomplex with an ELISA; wherein a decrease in the quantity of the immunocomplex in the test samples, as compared to the quantity of immunocomplexes formed under identical conditions with the same antibody and a control sample from one or more mammals known to have a lower degree of radiation injury or exposure, indicates a higher degree of radiation injury and exposure to the mammal The citrullinated proteins that can be measured by the methods of the invention include those selected from the group consisting of trichohyalin, keratin, filaggrin, myelin basic protein (MBP), and histones, such as H2X.

The methods of the invention can involve assessing radiation injury and exposure in mammals, including humans. Test samples taken from a mammal for measurement of citrullinated proteins include selected from the group consisting of blood, plasma, serum, skin, tissue, and urine. The methods of the invention can be used to assess radiation injuries such as small bowel damage, including damage that leads to epithelial cell loss.

In some embodiments, the methods further comprise measuring the level of at least one hematological parameter in the one or more test samples, wherein a decreased amount of citrullinated proteins and decreased level of at least one hematological parameter in the test samples, as compared to a control sample from one or more mammals known to have a lower degree of radiation injury or exposure, indicates a higher degree of radiation injury and exposure to the mammal. The at least one hematological parameter can be peripheral cell counts, such as one or more of white blood cell levels, red blood cell levels, lymphocyte levels, and/or platelet levels.

In another aspect, the invention provides kits for assessing radiation injury and exposure in a mammal comprising antibodies specific to citrullinated proteins and reagents for conducting ELISA on one or more test samples from the mammal.

The various features of novelty which characterize the invention are pointed out with particularity in the claims annexed to and forming a part of this disclosure. For a better understanding of the invention, its advantages, and specific objects attained by its uses, reference is made to the accompanying drawings and descriptive matter in which preferred embodiments of the invention are illustrated.

DETAILED DESCRIPTION OF THE INVENTION

Figure 1:
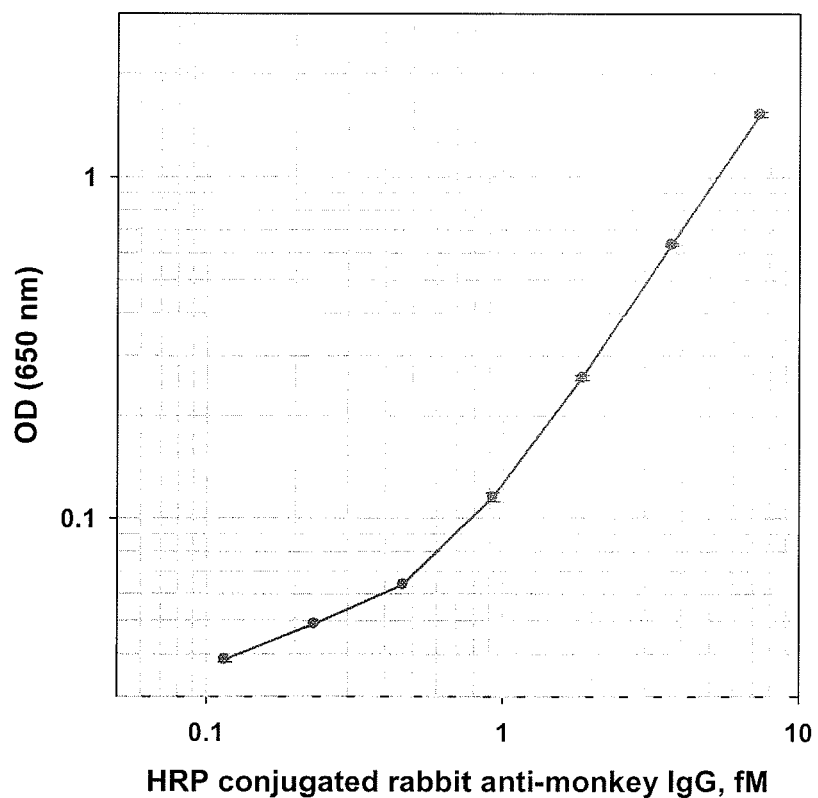
FIG. 1 shows a calibration curve for quantitation of HRP conjugated rabbit anti-monkey IgG detected with the ELISA methods of the invention.

For the purposes of promoting an understanding of the principles of the invention, reference will now be made to specific embodiments and specific language will be used to describe the same. It will nevertheless be understood that no limitation of the scope of the invention is thereby intended, such alteration and further modifications of the invention, and such further applications of the principles of the invention as illustrated herein, being contemplated as would normally occur to one skilled in the art to which the invention relates.

All terms as used herein are defined according to the ordinary meanings they have acquired in the art. Such definitions can be found in any technical dictionary or reference known to the skilled artisan, such as the *McGraw-Hill Dictionary of Scientific and Technical Terms* (McGraw-Hill, Inc.), *Molecular Cloning: A Laboratory Manual* (Cold Springs Harbor, N.Y.), *Remington's Pharmaceutical Sciences* (Mack Publishing, PA), and *Stedman's Medical Dictionary* (Williams and Wilkins, MD). These references, along with those references and patents cited herein are hereby incorporated by reference in their entirety.

Citrulline is a non-standard amino acid that is not normally present in proteins. Citrulline is generated as an intermediate in a metabolic pathway called the urea cycle, in which ornithine is converted to arginine. Citrulline is also formed during the production of nitric oxide. The amino acid citrulline is required to detoxify the liver from ammonia, which is a waste product of the body from oxidation. Citrulline promotes energy and assists with the immune system. This unusual amino acid is formed in the urea cycle by the addition of carbon dioxide and ammonia to ornithine. It is then combined with aspartic acid to form arginosuccinic acid, which later is metabolized into the amino acid arginine.

Citrulline malate (Stimol) has been shown to be a successful therapeutic in humans (Callis et al., 1991; Vanuxem et al. 1986; Bendahan et al., 2002) and animal models (Giannesini et al., 2009; Verleye et al., 1995). Callis and colleagues showed that citrulline malate stimulates hepatic ureogenesis and the renal reabsorption of bicarbonates. These metabolic actions had a protective effect against acidosis and ammonia poisoning and might explain the anti-fatigue properties of citrulline malate in man (Callis et al., 1991). Successful therapeutic effects have also been demonstrated using citrulline malate (Stimol) as an anti-fatigue compound in treatment of fatigue syndrome in cleanup workers of the sequelae of the Chernobyl Nuclear Power accident (Demina et al., 1999).

Citrulline metabolism falls into two categories: free citrulline and citrullinated proteins. Although citrulline cannot be incorporated into proteins during protein synthesis, some proteins contain citrulline residues (Rogers 1962). These proteins are modified post-translationally, by the conversion of arginine residues to citrulline. The fact that this amino acid is present in various tissues and is active on many proteins suggests it may have an important biological role. Insufficiencies in protein citrullination occur in some autoimmune diseases such as rheumatoid arthritis, psoriasis or multiple sclerosis (Curis et al. 2005). In particular, several experimental results suggest that the immune response to citrulline could play a significant role in the pathogenesis of rheumatoid arthritis inflammation (Hill et al. 2004). The best-known cases of citrullinated proteins include the proteins that are involved in epidermal keratinization (trichohyalin, keratin and filaggrin) (Rogers 1997, Kann et al. 2000, Ishigami et al. 2002) and the basic myelin protein, which makes up to 35% of the proteic component of the central nervous system (Wood et al. 1989, Ishiyama et al. 2001). Less well documented cases include citrullination of B23 nucleophosmin and some histones in leukocyte nuclei (Nakashima et al. 1999, Hagiwara et al. 2002) and PAD I activity in decidual cells of the female genital system (Arai et al. 1995). Histones are the chief protein components of chromatin and play an important role in gene regulation. An exemplary histone is H2X, which binds to a DNA with double strand breaks and marks the region undergoing DNA repair.

Plasma citrulline, a nonprotein amino acid produced by enterocytes, was suggested as a marker of remnant enterocyte mass in patients with short bowel. Crenn and colleagues evaluated citrulline as a marker of severity and extent of villous atrophy in patients without intestinal resection. In patients with villous atrophy diseases, plasma citrulline concentration may prove to be a simple and reliable marker of reduced enterocyte mass (Crenn et al. 2003).

The damage to the epithelial lining cells results in the loss of the natural barrier between intestinal microbes and the body, making it susceptible to systemic infections, fluid imbalances and losses, bloody diarrhea, colitis, and a host of other clinical signs, depending on radiation dose (Gillett et al., 1987; Hahn et al. 1975; Buell et al. 1989). The small bowel is a major dose-limiting organ with regard to both acute and late treatment-related morbidity when abdominal or pelvic cancers are treated with radiotherapy. Small bowel irradiation results in epithelial cell loss and consequently impairs function and metabolism.

Lutgens and colleagues demonstrated that after single-dose whole body irradiation (WBI) plasma citrulline level kinetics are dose-dependent and in accordance with radiation injury to the clonogenic compartment of small intestinal epithelium. Citrullinemia is a simple and sensitive marker for monitoring small bowel epithelial radiation damage after single WBI doses between 8-12 Gy. Furthermore, this parameter enables quantification of epithelial cell loss after doses per fraction between 3-12 Gy. A strong correlation of citrullinemia with mucosal surface lining and jejunal crypt regeneration has been found in mice subjected to WBI. The kinetics observed for this parameter support its use as an assay for monitoring epithelial radiation-induced intestinal damage in clinical practice (Lutgens et al. 2003).

As detailed above, protein citrullination is implicated in many different indications. An assay for measuring citrullinated proteins, such as the novel ELISA assay described herein, can be useful in the assessment of these different indications.

In some embodiments of the invention, the assay for measuring citrullinated proteins is useful for the assessment of radiation injury and exposure, and can be used in the novel methods described herein. Radiation injuries that can be assessed with the invention include injuries due to exposure to non-ionizing radiation or ionizing radiation, such as alpha radiation, beta radiation, gamma radiation, X-ray radiation, ultraviolet radiation, and/or neutrons. Scenarios involving radiation injury and exposure can involve radiological hazards such as nuclear detonations, covert placement of radioactive substances, and dirty bombs. At doses above about 1 Gy (gamma or X-rays) in humans, hematopoietic function is compromised, leading to decreases in white blood cell counts and increases susceptibility to infection (AFFRI 2003). At doses above 2 Gy, some mortality is likely (AFFRI 2003). The acute consequences of exposures between about 1 and 8 Gy are termed "hematopoietic syndrome," while the acute effects after doses of about 8 to 20 Gy are known as "GI syndrome," and effects after doses of about 20-30 Gy include gastrointestinal and cardiovascular damage with death occurring within 2-5 days.

The methods of the invention comprise obtaining one or more samples from a mammal, measuring the amount of citrullinated proteins in test samples from the mammal, and correlating the amount with an assessment of radiation injury and exposure, such that a decreased amount of citrullinated proteins in the test samples, as compared to a control sample from one or more mammals known to have a lower degree of radiation injury or exposure, indicates a higher degree of radiation injury and exposure to the mammal. In some embodiments, the control sample from one or more mammals known to have a lower degree of radiation injury or exposure includes a sample from one or more healthy mammals known to have no radiation injury.

In some embodiments, measuring the amount of citrullinated proteins comprises the steps of: contacting the test samples with an antibody immunoreactive with a citrullinated protein to form an immunocomplex; and detecting the immunocomplex with an enzyme-linked immunosorbent assay (ELISA); wherein a decrease in the quantity of the immunocomplex in the test samples, as compared to the quantity of immunocomplexes formed under identical conditions with the same antibody and a control sample from one or more mammals known to have a lower degree of radiation injury or exposure, indicates a higher degree of radiation injury and exposure to the mammal.

In general, the methods of the invention include obtaining a sample and contacting the sample with an antibody immunoreactive with a citrullinated protein under conditions effective to allow the formation of immunocomplexes. The methods include methods for detecting or quantifying the amount of citrullinated proteins in a sample, via the detection or quantitation of any immune complexes formed during the binding process, using an ELISA method. ELISA methods provide rapid, sensitive, and cost effective analyses of citrullinated proteins. In addition, the ELISA method is targeted to detect citrullinated proteins, rather than free citrulline, in the test sample, due to the small size of citrulline.

In terms of antigen detection, the test sample analyzed may be any sample that is suspected of containing a citrullinated protein, including, but are not limited to, blood, plasma, serum, skin, urine, hair follicles, and other accessible tissues. The sample can be taken from any mammal, including humans, mice, rats, and nonhuman primates. In some embodiments, the assessment of radiation injury and exposure made possible by the invention includes the quantitation and monitoring of epithelial radiation-induced small bowel damage.

Contacting the test sample with the antibody under conditions effective and for a period of time sufficient to allow the formation of immune complexes (primary immune complexes) is generally a matter of adding the composition to the sample and incubating the mixture for a period of time long enough for the antibodies to form immune complexes with, i.e., to bind to, any antigens present. After this time, the sample-antibody composition, such as a tissue section or ELISA plate, will generally be washed to remove any non-specifically bound antibody species, allowing only those antibodies specifically bound within the primary immune complexes to be detected. The antibody employed in the detection may itself be linked to a detectable label, wherein one would then detect this label, thereby allowing the amount of the primary immune complexes in the composition to be determined.

Alternatively, the first added component that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

In the clinical diagnosis or monitoring of patients exposed to radiation, the detection of reduced levels of citrullinated proteins, in comparison to the levels in a corresponding test sample from a control subject, is indicative of the extent of the patient's exposure to radiation. The basis for such diagnostic methods lies, in part, with the finding that the amount of citrullinated proteins is lower in samples from mammals exposed to higher levels of radiation (see Examples below).

In some embodiments, enzyme-linked immunosorbent assays (ELISA) in various formats are provided by the invention. In one exemplary ELISA, antibodies to citrullinated proteins are immobilized onto a selected surface exhibiting protein affinity, such as a well in a polystyrene microtiter plate. Then, a test sample, such as a clinical sample, containing the antigen is added to the wells. After binding and washing to remove non-specifically bound immunocomplexes, the bound antigen may be detected. Detection is generally achieved by the addition of a second antibody specific for the target protein, that is linked to a detectable label. This type of ELISA is a "sandwich ELISA". Detection may also be achieved by the addition of a second antibody, followed by the addition of a third antibody that has binding affinity for the second antibody, with the third antibody being linked to a detectable label. Color formation is monitored spectophotometrically and related to concentration of antigen by calibration to a standard curve.

In another exemplary ELISA, the test samples are immobilized onto the well surface and then contacted with the antibodies to citrullinated proteins. After binding and washing to remove non-specifically bound immunocomplexes, the bound antigen is detected. Where the initial antibodies are linked to a detectable label, the immunocomplexes may be detected directly. Again, the immunocomplexes may be detected using a second antibody that has binding affinity for the first antibody, with the second antibody being linked to a detectable label.

Another ELISA in which the citrullinated proteins are immobilized, involves the use of antibody competition in the detection. In this ELISA, labelled antibodies are added to the wells, allowed to bind to citrullinated proteins, and detected by means of their label. The amount of citrullinated proteins in a sample is then determined by mixing the sample with the labeled antibodies before or during incubation with coated wells. The presence of citrullinated proteins in the sample acts to reduce the amount of antibody available for binding to the well and thus reduces the ultimate signal.

Irrespective of the format employed, ELISAs have certain features in common, such as coating, incubating or binding, washing to remove non-specifically bound species, and detecting the bound immunocomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can be used rather than a direct procedure. Thus, after binding of a protein or antibody to the well, coating with a non-reactive material to reduce background, and washing to remove unbound material, the immobilizing surface is contacted with the control or test sample to be tested under conditions effective to allow immunocomplex (antigen/antibody) formation. Detection of the immunocomplex then requires a labeled secondary binding ligand or antibody, or a secondary binding ligand or antibody in conjunction with a labeled tertiary antibody or third binding ligand.

"Under conditions effective to allow immunocomplex formation" means that the conditions include diluting the antigens and antibodies with solutions such as BSA, bovine gamma globulin (BGG) and phosphate buffered saline (PBS)/ TWEEN® (polysorbate). These added agents can assist in the reduction of nonspecific background.

The "suitable" conditions also mean that the incubation is at a temperature and for a period of time sufficient to allow effective binding. Incubation steps are typically from about 1 to 2 to 4 hours, at temperatures such as on the order of 25° to 27° C., or may be overnight at about 4° C. or so.

Following all incubation steps in an ELISA, the contacted surface is washed so as to remove non-complexed material. An exemplary washing procedure includes washing with a solution such as PBS/TWEEN® (polysorbate), or borate buffer. Following the formation of specific immunocomplexes between the test sample and the originally bound material, and subsequent washing, the occurrence of even minute amounts of immunocomplexes may be determined.

To provide a detecting means, the second or third antibody will have an associated label to allow detection. In some embodiments, the label is an enzyme that will generate color development upon incubating with an appropriate chromogenic substrate. Thus, for example, first or second immunocomplex may be incubated with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-TWEEN® (polysorbate)).

After incubation with the labeled antibody, and subsequent to washing to remove unbound material, the amount of label is quantified, e.g., by incubation with a chromogenic substrate such as urea and bromocresol purple or 2,2'-azido-di-3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

Commercially available antibodies that are useful for the methods of the invention include, but are not limited to, those listed in Table 1.

TABLE 1

Antibodies for ELISA

| | Antibody | Catalog # | Commercial Source |
|---|---|---|---|
| 1 | rabbit polyclonal anti-citrulline | 231246 | Calbiochem, Inc., San Diego, CA |
| 2 | rabbit polyclonal anti-citrulline | Ab6464 | Abcam Inc., Cambridge, MA |
| 3 | rabbit polyclonal anti-citrulline | 5612 | Millipore (Chemicon), Inc., Temecula, CA |
| 4 | HRP conjugated rabbit anti-monkey IgG | RRHG-65P | ICL, Inc., Newberg, OR |
| 5 | HRP conjugated rabbit anti-mouse IgG | 315-035-003 | Jackson Immuno Research Laboratories, Inc., West Grove, PA |
| 6 | HRP conjugated rabbit anti-rat IgG | 312-035-003 | Jackson Immuno Research Laboratories, Inc., West Grove, PA |

In further embodiments, the invention provides kits for use with the methods described above. The kits may comprise, in suitable container means, an antibody to citrullinated proteins, and reagents for conducting an immunoassay. In certain embodiments, the antibody that binds to citrullinated proteins may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the kits include the two-component reagent that comprises a secondary antibody that has binding affinity for the first antibody or antigen, along with a third antibody that has binding affinity for the second antibody, the third antibody being linked to a detectable label.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, and may be suitably aliquoted. Where a second or third binding ligand or additional component is provided, the kit will also generally contain a second, third or other additional container into which this ligand or component may be placed.

In further embodiments, the invention provides methods of assessing radiation injury and exposure in a subject comprising measuring the amount of citrullinated proteins and at least one hematological parameter in a test sample, wherein a decreased amount of citrullinated proteins and decreased level of at least one hematological parameter in the test samples, as compared to a control sample from one or more mammals known to have a lower degree of radiation injury or exposure, indicates a higher degree of radiation injury and exposure to the mammal.

The use of hematological and serum enzyme activity parameters, evaluated in the early time frame after a suspected radiation exposure, in combination with the determined amounts of citrullinated proteins in a sample can enhance radiation exposure discrimination and assessment (Ossetrova et al. 2007). Examples of hematological parameters that can be evaluated include peripheral cell counts such as, for example, one or more of white blood cell levels, red blood cell levels, lymphocyte levels, and/or platelet levels.

The methods of the invention include assessment of other diagnostic information indicative of radiation exposure. For example, in addition to hematological parameters, assessment of physiological signs and symptoms exhibited by the subject and an estimate of the dose of radiation that the subject was exposed to can be integrated with results of amounts of citrullinated proteins to improve the assessment of radiation injury and exposure. Physiological signs and symptoms that may be indicative of radiation exposure include signs and symptoms relating to the subject's neurovascular system (e.g. nausea, vomiting, anorexia, fatigue syndrome, fever, headache, hypotension, neurological deficits, cognitive deficits), hematopoietic system (e.g. lymphocyte changes, granulocyte changes, thrombocyte changes, blood loss, infection), cutaneous system (e.g. erythema, sensation/itching, swelling/edema, blistering, desquamation, ulcer/necrosis, hair loss, onycholysis), and/or gastrointestinal system (e.g. diarrhea, abdominal cramps/pain). An estimate of the dose of radiation that the subject was exposed to can be obtained, for example, by physical dosimetry based on personnel dosimeter or location-based estimates. Body weight loss is another physiological parameter that is correlated with radiation injury and exposure, including gastrointestinal injuries. Any method of assessing radiation injury and exposure comprising measuring the amounts of citrullinated proteins combined with assessing one or more other diagnostic parameters indicative of radiation exposure is contemplated by the invention.

Reference will now be made to specific examples illustrating the constructs and methods above. It is to be understood that the examples are provided to illustrate preferred embodiments and that no limitation to the scope of the invention is intended thereby.

EXAMPLES

The aim of this study was to determine the effect of whole-body radiation on circulating levels of citrullinated proteins in nonhuman primates (NHP). In this study, animals were exposed to 7.2-12.5 Gy whole-body 6 MV LINAC x-radiation. Plasma citrullinated proteins were measured using newly developed sandwich enzyme linked immunosorbent assay (ELISA).

The results demonstrate that plasma levels of citrullinated proteins were affected by total-body irradiation (TBI). Plasma citrullinated protein levels were significantly decreased to 20% and 50% compare to pre-irradiation levels at 1 and 2 days after irradiation to 7.2 Gy, respectively. At 20 days after irradiation, plasma citrullinated protein levels returned to normal in NHPs that survived exposure. Citrullinated protein levels in NHPs exposed to 12 Gy dramatically decreased because of GI syndrome and at the eleventh day reached the level of 7% compared to pre-TBI levels. Radiation-induced changes in citrullinated proteins were most pronounced at 2 days postirradiation. The results showed strong correlations between citrullinated protein levels and blood cell populations, as well as percentage of body weight loss in animals.

Materials and Methods

A. Model System, Radiation Exposure, and Peripheral Blood Biosampling

Domestic-born, male rhesus monkeys, *Macaca mulatta*, 4.8±0.7 kg, were housed in individual stainless steel cages in conventional holding rooms at the University of Maryland's Veterinary Resources Department in an animal facility accredited by the Association for the Assessment and Accreditation of Laboratory Animal Care International (AAALAC). Monkeys were provided 10 air changes of 100% fresh air, conditioned to (72±2)° F. with a relative humidity of (50±20) % and maintained on a 12-hour light/dark full spectrum light cycle, with no twilight. Monkeys were provided with commercial primate chow, supplemented with fresh fruit and tap water ad libitum. Research was conducted according to the principles enunciated in the *Guide for the Care and Use of Laboratory Animals*, prepared by the Institute of Laboratory Animal Resources, National Research Council, and under an IACUC approved protocol. Rhesus monkeys received TBI to a midline tissue dose from 7.2 to 12 Gy, 6 MV LINAC x-irradiation at 0.8 Gy $min^{-1}$. Following irradiation, animals were monitored for complete blood counts, body weight, temperature, and hydration status for 60 days. Animals were administered medical management consisting of intravenous fluids, antibiotics (when absolute neutrophil counts <500/μL), blood transfusions, and other support as required. Animals received full supportive care compatible to standards applicable to human care.

Ketamine-anesthetized animals (Ketaset® [10 mg $kg^{-1}$, i.m.], Fort Dodge Laboratories; Fort Dodge, Ind.) were placed in a plexiglass restraint chair (to which they had been previously prehabituated), allowed to regain consciousness, and x-irradiated in the posterior-anterior direction, then rotated at mid-dose to the anterior-posterior direction to complete the exposure. Dosimetry was performed using paired 0.5-$cm^3$ ionization chambers, with calibration factors traceable to the National Institute of Standards and Technology.

Following irradiation, animals were monitored for complete blood counts, body weight, temperature, and hydration status for 60 days. Animals received full supportive care compatible to standards applicable to human care. Animals were administered medical management consisting of intravenous fluids, antibiotics (when absolute neutrophil counts (ANC)<500/μL), blood transfusions, and other support as required.

Before the study (prior TBI) and then at designated times after irradiation, peripheral blood was drawn from ketamine-anesthetized macaques by saphenous vein into serum separator (Becton, Dickinson and Company, Franklin Lakes, N.J.) and potassium EDTA (Becton, Dickinson and Company, Franklin Lakes, N.J.) vacutainer tubes. Peripheral complete blood cell count (CBC) and differentials were determined using a clinical hematology analyzer (Bayer Advia 120, Bayer, Tarrytown, N.Y.) for 60 days post-TBI. Tubes with collected peripheral blood for ELISA citrullinated protein measurements were centrifuged at 800 g for 10 min, and plasma was collected and preserved at −80° C.

B. Protein Bioassays

Plasma citrullinated protein measurements were performed using a sandwich ELISA. Samples were assayed for colorimetric detection and quantitation of total protein via the bicinchoninic acid (BCA) method (Pierce) prior to the immunoassay. Rabbit polyclonal anti-citrulline (Cat. #231246, Calbiochem, Inc., San Diego, Calif.) was diluted to a working concentration 1 $\mu ml^{-1}$ in phosphate-buffered saline (PBS) and incubated overnight at 4° C. After a wash step with 0.05% TWEEN® 20 (polysorbate 20) in phosphate-buffered saline (PBS), plates were blocked by adding 200 μl of blocking buffer (2% bovine serum albumin (BSA) in PBS) to each well and incubated for 40 min at room temperature. Plasma samples and standards (100 μl per each well) were diluted in assay buffer (1% BSA in PBS) and incubated 2 h at room temperature. After a wash step, detection antibody HRP-conjugated rabbit anti-monkey IgG (Cat. #RRHG-65P, ICL, Inc.) diluted in assay buffer to the working concentration 200 ng/ml, was diluted (1:5000) in assay buffer (PBS, 1% BSA), added to each well, and incubated for 1 h at room temperature. After a final wash step, the K-Blue substrate (Cat. #308176, Neogen Corporation, Lexington, Ky.) was added per manufacture guidance for color development. The reaction was stopped after 30 min using a stop solution (Cat. #301475, Neogen Corporation, Lexington, Ky.). The amount of color that developed was measured at 650 nm in a microtiter plate using a spectrophotometer (BIO-TEK Instruments, Inc., Winooski, Vt.). Three replicate measurements were determined for each sample and standards. Polystyrene 96-well microtiter plates (NUNC Brand Products, Nalge NUNC International, Rochester, N.Y.) were used to perform immunoassays. Citrullinated protein concentrations in plasma samples were determined via use of generated standard calibration curves for quantitation of antibody-antigen complexes.

C. Data Analysis

Statistical software, PC SAS, was used for statistical data analysis (SAS Institute Inc., 2000; Khattree et al., 2000). Two-sided Student's t test was used to make pairwise comparisons to evaluate the statistical significances between groups. Values of P<0.05 were considered statistically significant. Citrullinated protein concentrations in plasma samples were determined via use of Table Curve 2D software. Values were expressed as means±standard deviations (STD) for three replicate measurements. Correlation analysis was performed to describe the strength of association between citrullinated proteins and other biomarkers.

Results and Discussion

Figure 2:
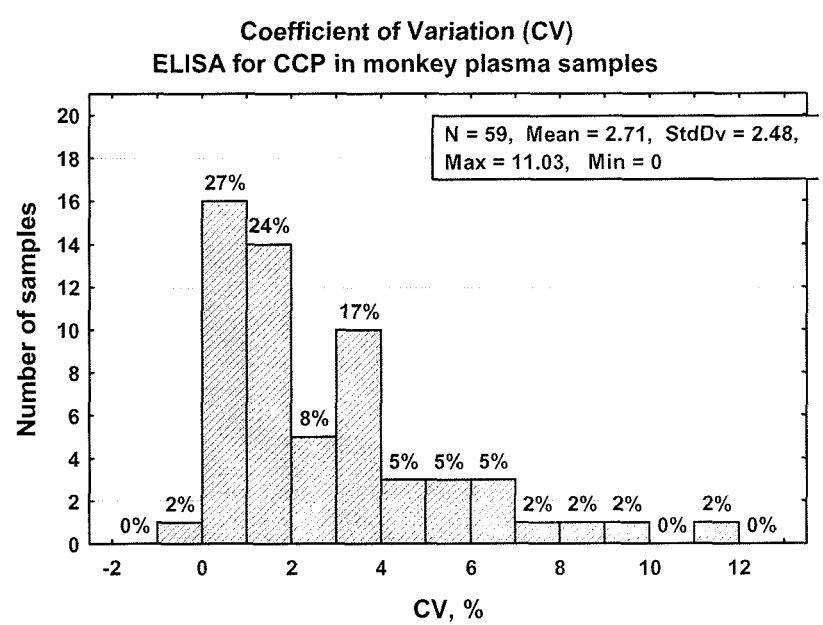
FIG. 2 shows a calculated precision profile (CV values) for measured citrullinated protein content in blood plasma of rhesus monkeys.

A calibration curve for quantitation of HRP conjugated rabbit anti-monkey IgG (detection antibody in sandwich ELISA format) prepared for serial dilutions is shown in FIG. 1. The linearity for the assay was demonstrated directly by serial dilutions of standard or antigen present in plasma samples. The response was directly proportional to the concentrations of the citrullinated proteins in plasma samples by means of a well-defined mathematical calculation. The calculated precision profile (CV values) for n=59 assayed NHP plasma samples demonstrates the good accuracy and reproducibility for sample measurements (FIG. 2). Mean and maximum CV is 2.7% and 11%, respectively.

Using the ELISA procedure, citrullinated protein content was measured in blood plasma of 5 male rhesus monkeys irradiated to 7.2 Gy 6 MV LINAC x-rays at dose rate 0.8 Gy/min at several sampling time-points before and after TBI. The results demonstrate that NHP plasma levels of citrullinated protein were affected by total-body irradiation (TBI) of animals.

Figure 3:
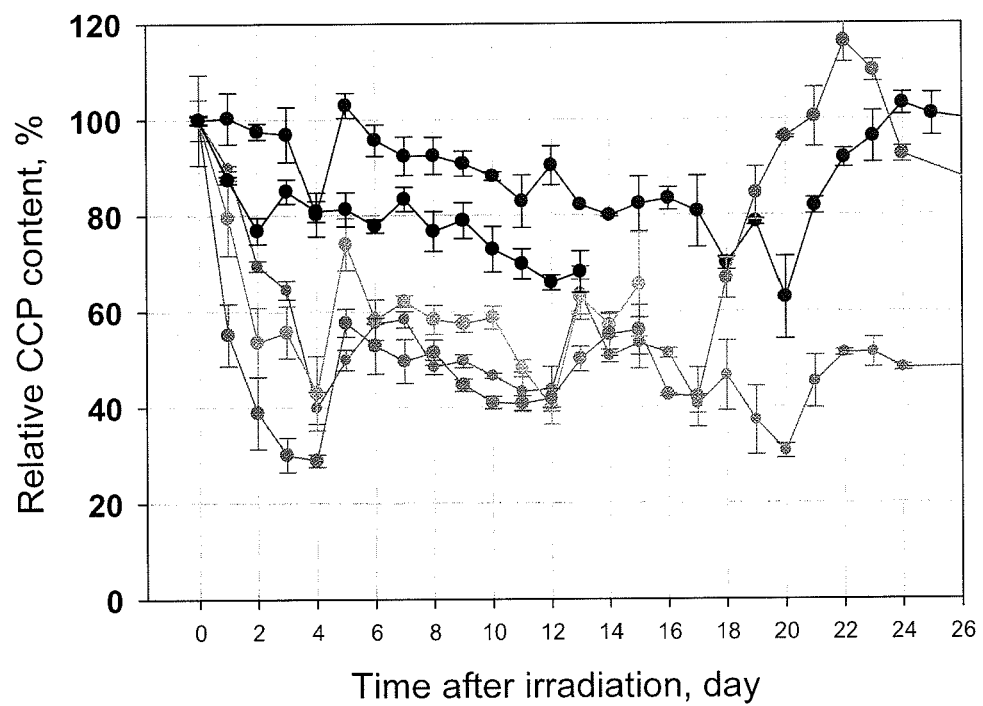
FIG. 3 shows a time course for relative citrullinated protein content (normalized on pre-TBI level) in blood plasma of 5 rhesus monkeys after TBI to 7.2 Gy 6 MV LINAC x-rays at 0.8 Gy/min; individual data for 01545 (closed circles), 02031 (closed triangles), 03967 (squares), 03R0733 (open circles), 03R0537 (open triangles).
Figure 4:
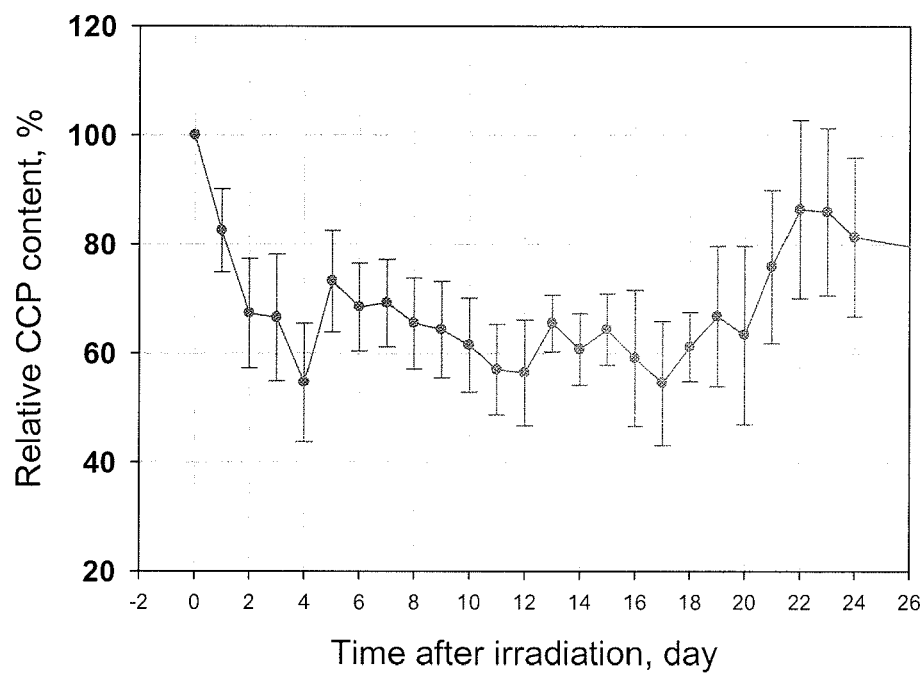
FIG. 4 shows a time course for relative citrullinated protein content (normalized on pre-TBI level) in blood plasma of 5 rhesus monkeys before and after TBI to 7.2 Gy 6 MV LINAC x-rays at 0.8 Gy/min (Mean±STD).

The results for time course of relative citrullinated protein content (normalized on pre-TBI level) in blood plasma of 5 male rhesus monkeys irradiated to 7.2 Gy are shown in FIG. 3 (individual data are expressed as means±STD calculated from tree runs of assayed samples) and FIG. 4 (means±STD for 5 animals). Baseline (pre-TBI) levels of citrullinated protein content in plasma of 7.2-Gy NHP cohort ranges from 1.20(±0.12) to 3.98(±0.01) fM $ml^{-1}$. In 3 of 5 monkeys, citrullinated protein content was decreased to (20±11) %; in animal 03R0733 to (55±4) %; and in animal 02031 there was no statistical significant difference at 1 day after TBI compare to the pre-TBI level. Radiation-induced changes in citrullinated proteins were most pronounced at 2 days postirradiation. In 2 of 5 monkeys (01545 and 03R0537), citrullinated protein content was decreased to (25±5) %; in animal 03967 to (45±5) %; in animal 03R0733 to (61±3) %; and in animal 02031 there was still no statistical significant difference at 2 days after TBI compare to the pre-TBI level. In two of three NHPs that survived exposure (03R0733 and 02031), plasma citrullinated protein levels returned to normal at 20 days and 24 days after TBI, respectively. In one animal (01545), citrullinated protein levels at 24 days after TBI was still decreased to (38.97±0.69) % compared to pre-TBI levels. Two of five NHPs (03R0537 and 03967) did not survive exposure because of hematopoeitic syndrome and were sacrificed at day 13 and day 15 after TBI, respectively. Plasma citrullinated protein levels in these NHPs were significantly decreased to (23.26±1.67) % and (24.8±4.21) % compared to pre-TBI, respectively.

The consequences of irradiation may manifest themselves either immediately or in the distant future. The early effects that radiation can include nausea, vomiting, diarrhea, general malaise, loss of appetite, fever, internal bleeding and hemorrhage, and decrease in the amount of white blood cells, which results in increased risk of infection and sometimes death. With supportive care, all animals in this study survived exposure. However, they manifested the loss of appetite during 5-6 days after TBI. In all five animals, plasma citrullinated protein levels decreased in a similar manner as plasma free citrulline concentrations reported by Cameron and colleagues, who investigated the metabolic differences in plasma of thirteen adult male macaques (*Macaca fascicularis*) in fed and fasted states at intervals between 1.5 and 52 h after the meal and reported that plasma free citrulline concentrations decreased from (40±2) nM mL$^{-1}$ to (24±2) nM mL$^{-1}$ during the (1.5-4) h interval and (40-52) h interval, respectively (Cameron et al., 1985).

Basic knowledge has been obtained concerning human and nonhuman physiologic and biochemical characteristics in order to establish relationships between these species in amino acid patterns and certain enzymatic activities (Peters et al. 1971; 1972; Chao et al., 1973; Cameron et al., 1985). Chao and colleagues reported that free citrulline levels in normal, fasting adults of three different monkey species range from (0.41±0.04) to (0.83±0.09) mg per 100 mL (Chao et al., 1973). Numerous studies to investigate the quantitative differences in plasma levels of amino acids and related compounds between macaques and humans showed that citrulline levels in rhesus monkeys were not significantly different from human levels (Peters et al. 1971; Chao et al., 1973).

Figure 5:
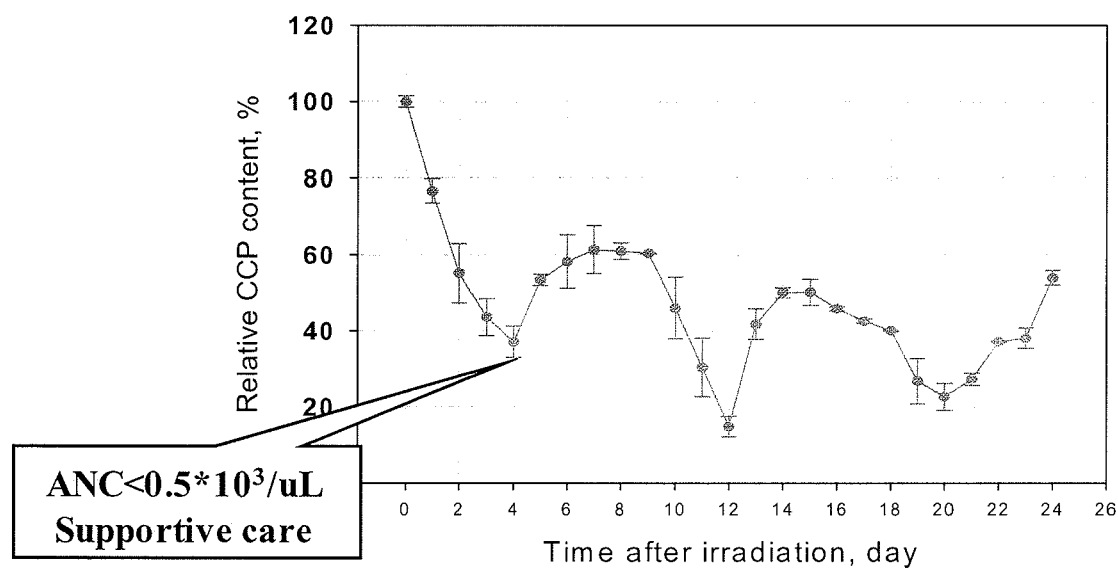
FIG. 5 shows a time course for relative citrullinated protein content (normalized on pre-TBI level) in blood plasma of rhesus monkeys before and after TBI to 8.9 Gy 6 MV LINAC x-rays at 0.8 Gy/min.

The time course of citrullinated protein content measured in the blood of rhesus monkey (03R0533) irradiated to 8.9 Gy LINAC x-rays before and up to 24 days after TBI is shown in FIG. 5. Pre-TBI levels of citrullinated protein content in plasma of this NHP was (3.29±0.07) fM ml$^{-1}$. Plasma citrullinated protein levels significantly (p<0.0006) decreased by (20.59±2.11) % at 1 day after irradiation. The animal survived exposure up to 60 days with full supportive care; however, citrullinated protein levels at 24 days after TBI was still significantly decreased (43.33±0.71) % compared to pre-TBI.

Figure 6:
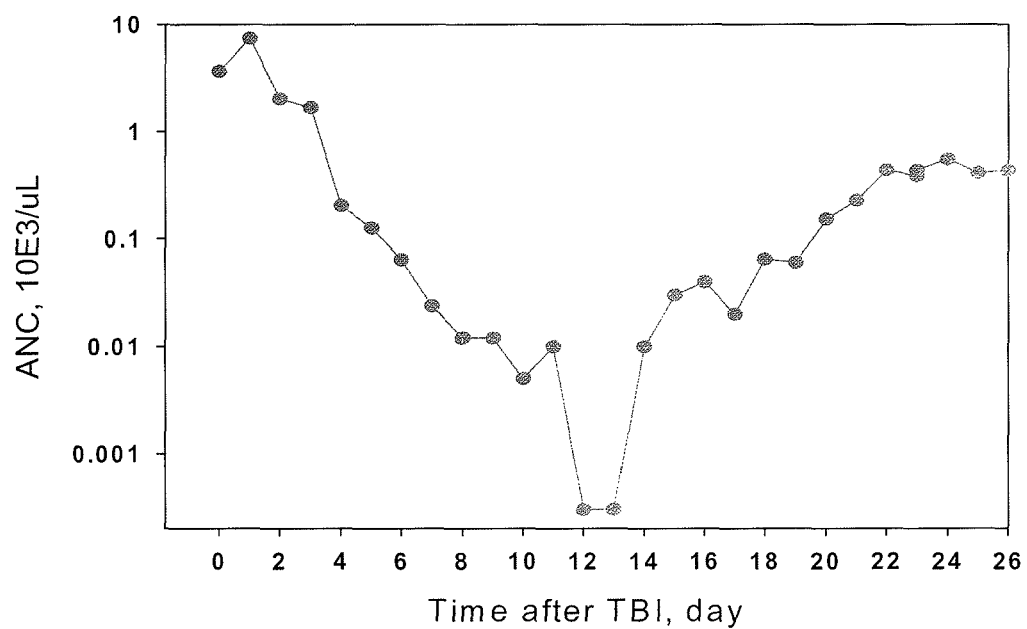
FIG. 6 shows a time course for absolute neutrophil counts (ANC) in blood of rhesus monkeys before and after TBI to 8.9 Gy 6 MV LINAC x-rays at 0.8 Gy/min.
Figure 7:
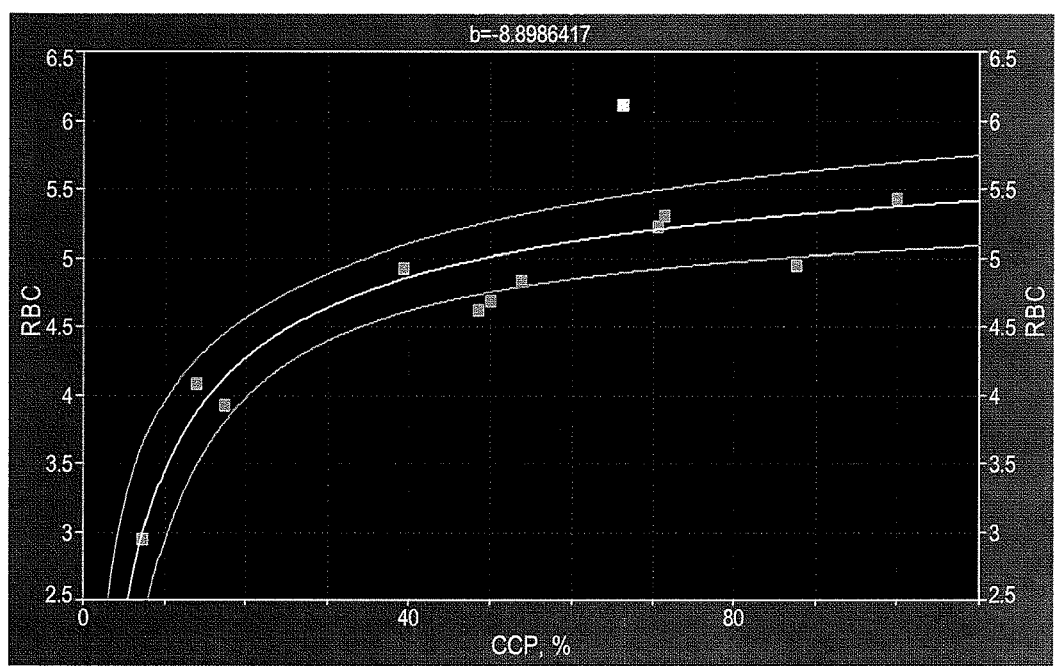
FIG. 7 shows a correlation between the relative citrullinated protein content and red blood cells (RBC) (R=0.899) after TBI to 8.9 Gy 6 MV LINAC x-rays at 0.8 Gy/min.

Whole body ionizing radiation causes defective hemopoiesis as a function of the radiation dose. Defective hemopoiesis results in a decline in all blood cell counts for several weeks after exposure. Strong correlations (R=0.821) were found between relative citrullinated protein content and absolute neutrophil counts (ANC) in plasma of the rhesus monkey. Severe neutrophenia (ANC=0.204×10$^9$/L) was observed at 4 days after irradiation. The minimum relative citrullinated protein content level of (0.26±0.12) fM ml$^{-1}$ (i.e., (7.95±3.71) % compared to pre-TBI level) (FIG. 5) coincided with the nadir of neutrophil counts observed on day 12 after TBI (FIG. 6). Citrullinated protein levels significantly (p<0.0001) decreased to (42.60±2.20) % at 24 days after TBI compared to pre-TBI. Strong correlations (R=0.899) were also found between relative citrullinated protein content and red blood cells (RBC) (FIG. 7).

The prodromal phase of GI syndrome is very abrupt in onset and characterized by nausea and diarrhea, which typically subsides after several days, followed by a short latent period. Symptoms then return, including white blood cell depression, nausea, vomiting, diarrhea (sometimes bloody), fever, and massive electrolyte imbalances, which ultimately will result in death.

Figure 8:
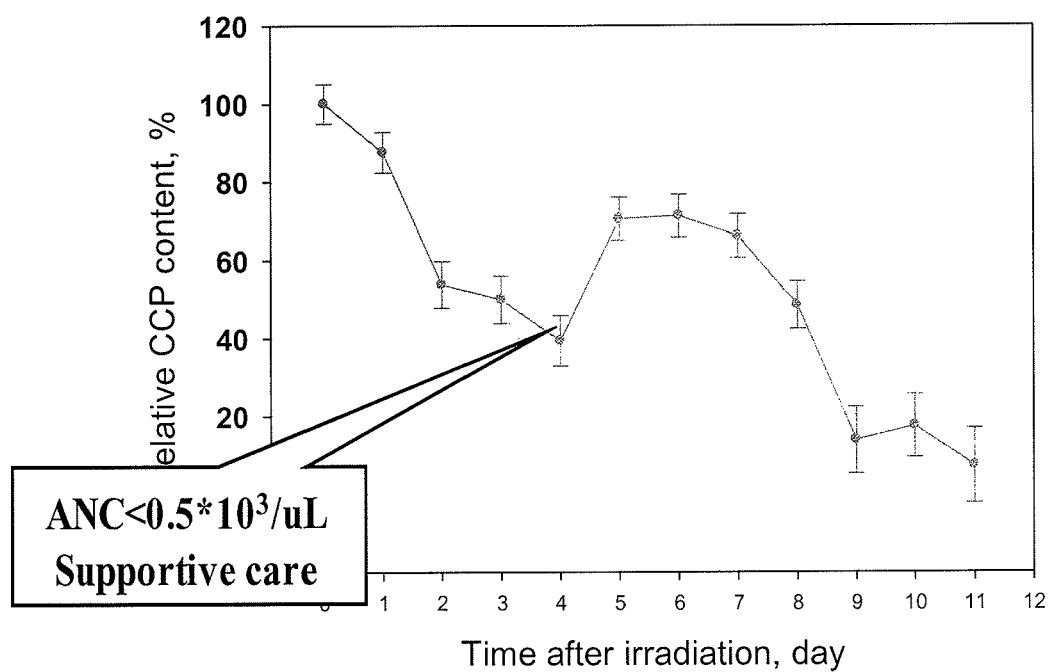
FIG. 8 shows a time course for relative citrullinated protein content (normalized on pre-TBI level) in blood plasma of rhesus monkeys before and after TBI to 12 Gy 6 MV LINAC x-rays at 0.8 Gy/min.

The time course of citrullinated protein content measured in blood of a rhesus monkey (R04065) irradiated to GI dose of 12 Gy LINAC x-rays before and up to 11 days after TBI is shown in FIG. 8. The animal did not survive exposure and was sacrificed 12 days after TBI. The pre-TBI level of citrullinated protein content in plasma of this NHP was (1.34±0.07) fM mL$^{-1}$. Plasma citrullinated protein levels significantly (p<0.006) decreased by (12.42±5.21) % at 1 day after irradiation. Severe neutrophenia (ANC=0.56×10$^9$/L) was observed at 4 days after irradiation. Citrullinated protein content decreased significantly (p<0.0003) at 4 days after TBI compared to the pre-TBI level, and increased on at 5 days after TBI due to beginning of supportive care and oral feeding. However, two days later, the level dramatically decreased because of GI syndrome and reached a level of 7% compared to the pre-irradiation level.

Figure 9:
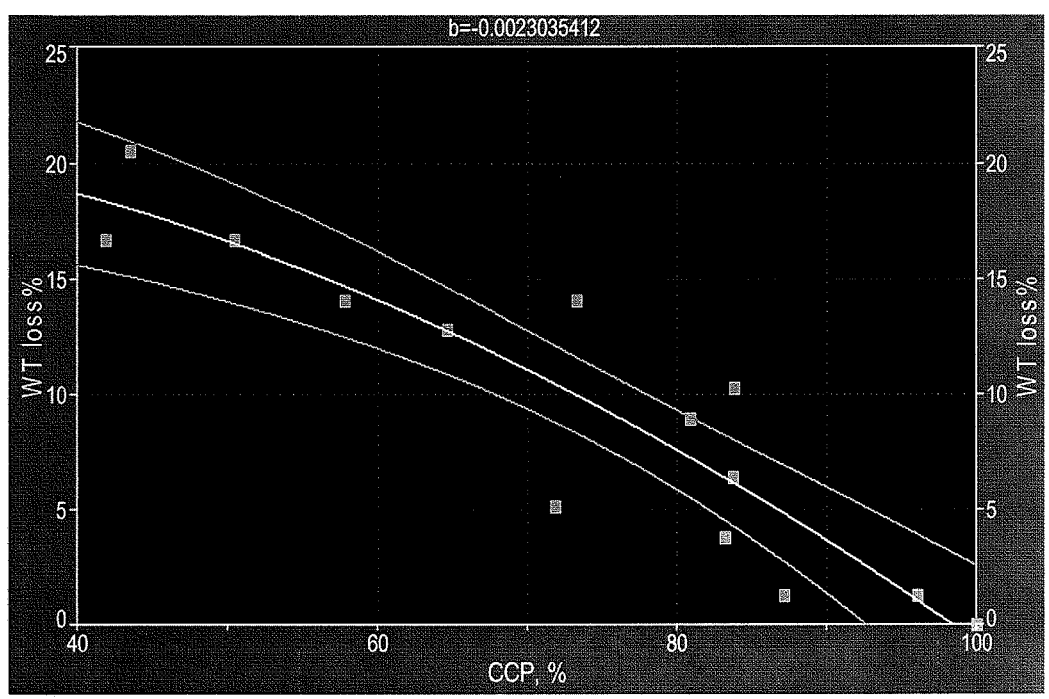
FIG. 9 shows a correlation between the relative citrullinated protein content and percentage of body weight loss (R=0.912) after TBI to 12 Gy 6 MV LINAC x-rays at 0.8 Gy/min.
Figure 10:
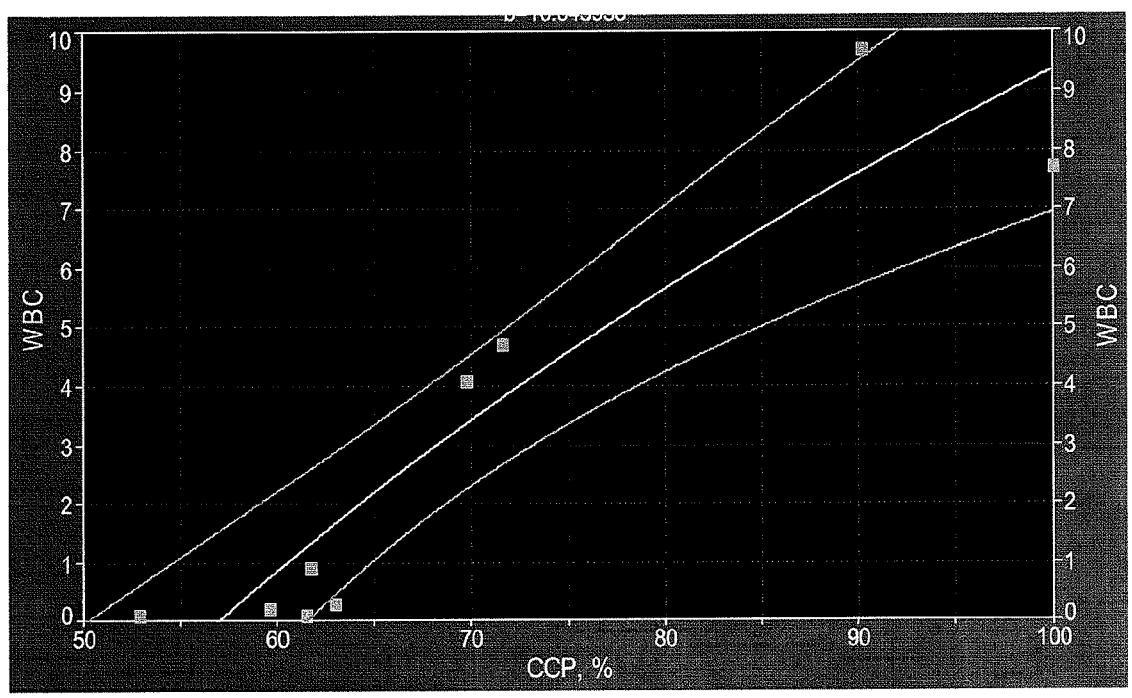
FIG. 10 shows a correlation between the relative citrullinated protein content and white blood cells (WBC) (R=0.933) after TBI to 12 Gy 6 MV LINAC x-rays at 0.8 Gy/min.
Figure 11:
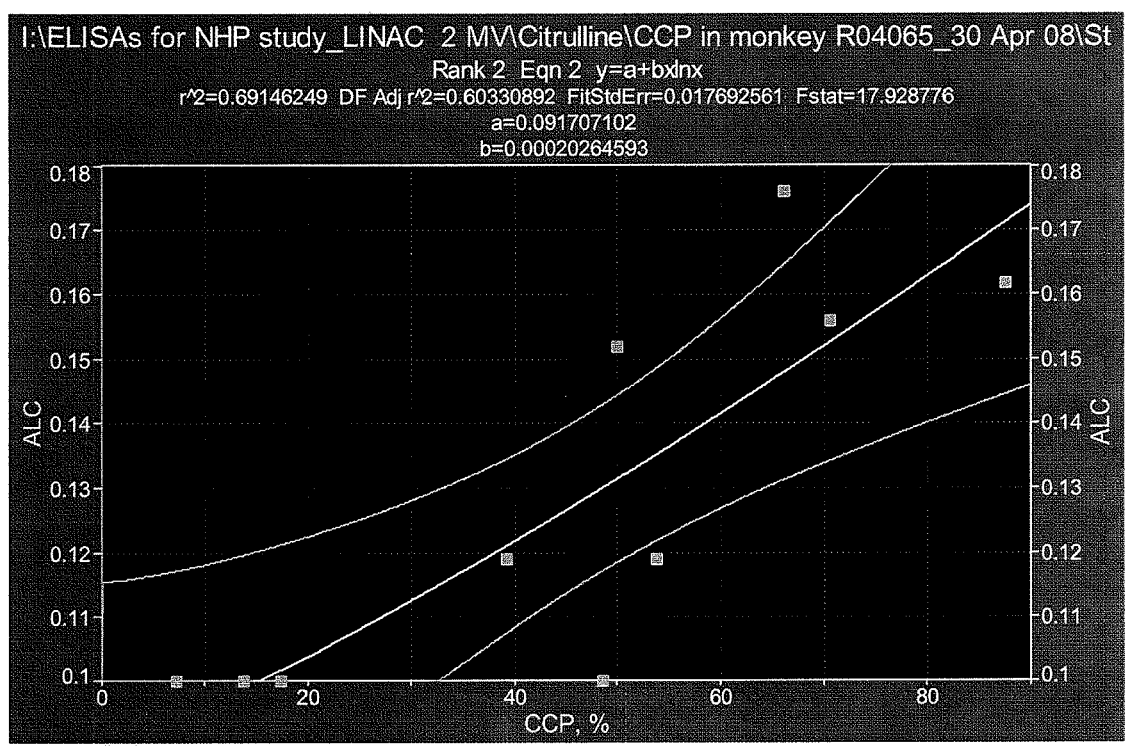
FIG. 11 shows a correlation between the relative citrullinated protein content and absolute lymphocyte counts (ALC) (R=0.885) in plasma of rhesus monkey R04065 irradiated to 12 Gy TBI.
Figure 12:
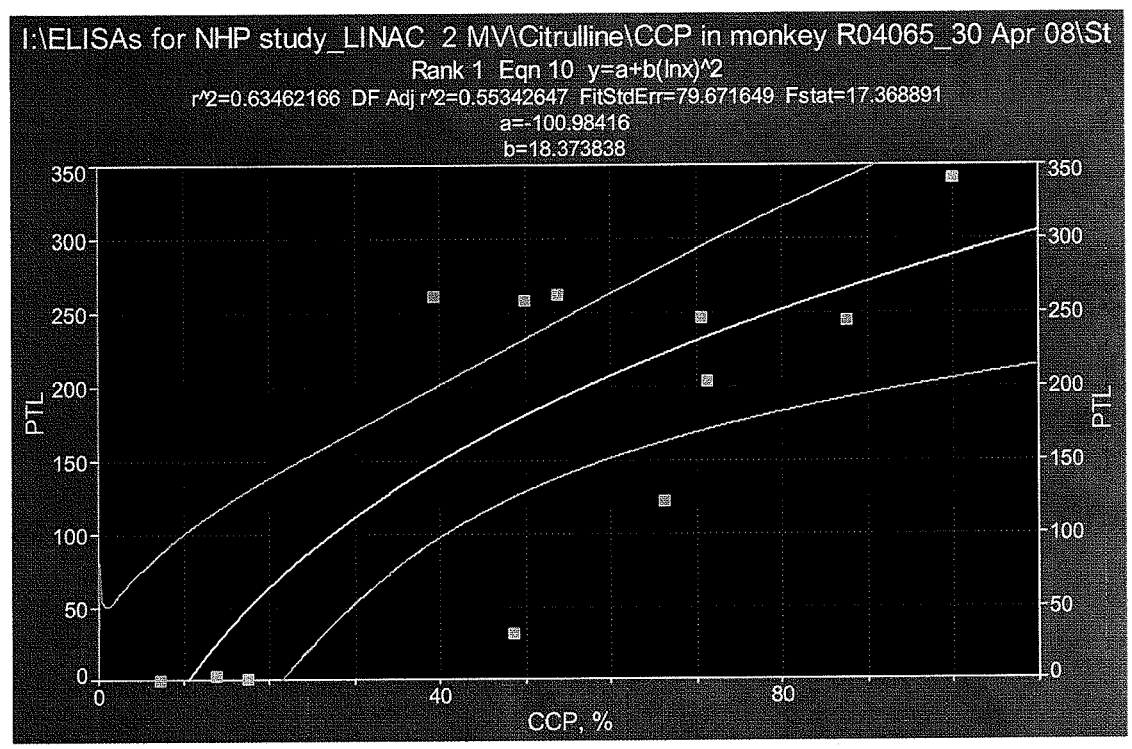
FIG. 12 shows a correlation between relative citrullinated protein content and platelets (PLT) (R=0.797) in plasma of rhesus monkey R04065 irradiated to 12 Gy TBI.

The results suggest that radiation-induced changes in citrullinated proteins are most pronounced at 2 days post-irradiation. Strong correlations (R=0.899) were found between relative citrullinated protein content and percentage of body weight loss (R=0.912; FIG. 9) as well as blood cell populations: white blood cells (R=0.973; FIG. 10), lymphocytes (R=0.885; FIG. 11) and platelets (R=0.797; FIG. 12).

The results from this study demonstrate for the first time that citrullinated proteins in blood plasma of irradiated animals show promise as a prognostic factor of radiation-induced small bowel damage, and that the novel ELISA is a sensitive method to detect these metabolic changes. The use of non-human primate (NHP) model systems to validate suitable medical countermeasures and novel biodosimetric approaches is clearly recognized by the scientific community (Stone et al., 2004). Nonhuman primates exhibit a similar profile survival time dose response as humans (Dixon, 1985).

While the foregoing specification teaches the principles of the invention, with examples provided for the purpose of illustration, it will be appreciated by one skilled in the art from reading this disclosure that various changes in form and detail can be made without departing from the true scope of the invention.

REFERENCES

AFRRI-Armed Forces Radiobiology Research Institute. Medical Management of Radiological Casualties. (Available on the world wide web at afrri(dot)usuhs(dot)mil(dot) www(dot)outreach(dot)mmoresources(dot)htm (2003).

Arai T, Kusubata M, Kohsaka T, Shiraiwa M, Sugawara K, Takahara H. 1995. Mouse uterus peptidylarginine deiminase is expressed in decidual cells during pregnancy. J Cell Biochem 58(3): 269-278.

Bendahan D, Mattei J P, Ghattas B, Confort-Gouny S, Le Guern M E, Cozzone P J. 2002. Citrulline/malate promotes aerobic energy production in human exercising muscle. British Journal of Sports Medicine 36(4):282-289.

Blijlevens N M, Lutgens L C, Schattenberg A V, Donnelly J P. 2004. Citrulline: a potentially simple quantitative marker of intestinal epithelial damage following myeloablative therapy. Bone Marrow Transplant. 34(3):193-6.

Buell M G, Harding R K. 1989. Proinflammatory effects of local abdominal irradiation on rat gastrointestinal tract. Dig Dis Sci 34(3): 390-399.

Callis A, Magnan de Bornier B, Serrano J, Serrano J J, Bellet H, Saumade R. 1991. Activity of Cirruline malate on acid-base balance and blood ammonia and amino acid levels// Arzneimittel-Forschung/Drug Research, 41(6): 660-663.

Cameron J L, Koerker D J, and Steiner R A. 1985. Metabolic changes during maturation of male monkeys: possible signals for onset of puberty. *Am J Physiol Endocrinol Metab* 249: E385-E391.

Chao W R, Berridge B J Jr, Peters J H. 1973. Amino acid levels in the plasma of fasting macaques (*Macaca cyclopis, M. fascicularis,* and *M. mulatta*). Laboratory Animal Science, 23(3):380-384.

Curis E, Nicolis I, Moinard C, Osowska S, Zerrouk N, Benazeth S, Cynober L. 2005 Almost all about citrulline in mammals. Amino Acids NIL.

Demina M V, Zemtsova N A, Muromtseva G A. 1999. Treatment of fatigue syndrome in the cleanup workers of the sequelae of the accident at the Chernobyl Atomic Electric Power Station. The Practitioner 1: 56-57 (in Russian).

Dixon B. 1985. The biological and clinical effects of acute whole or partial body irradiation. J. Soc. Radiol. Prot. 5(3): 121-128.

Hahn F F, Barnes J E, Hobbs C H, and Mauderly J L. 1975. Effect of $^{90}$Y Inhaled in fused clay particles on the gastrointestinal tract of Beagles. Radiation Research 61: 444-456.

Hagiwara T, Nakashima K, Hirano H, Senshu T, Yamada M. 2002. Deimination of arginine residues in nucleophosmin/ B23 and histones in HL-60 granulocytes. Biochem Biophys Res Commun 290(3): 979-983.

Hill J, Cairns E, Bell D A. 2004. The joy of citrulline: new insights into the diagnosis, pathogenesis, and treatment of rheumatoid arthritis. J Rheumatol 31(8): 1471-1473.

Giannesini B, Izquierdo M, Le Fur Y, Cozzone P J, Verleye M, Le Guern M E, Gillardin J M, Bendahan D. 2009. Beneficial effects of citrulline malate on skeletal muscle function in endotoxemic rat. European Journal of Pharmacology 602(1): 143-147.

Gillett N A, Muggenburg B A, Boecker B B, et al. 1987. Single inhalation exposure to $^{90}$SrCl$_2$ in the beagle dog: Hematological effects. Radiation Research 110: 267-288.

Ishiyama N, Bates I R, Hill C M, Wood D D, Matharu P, Viner N J, Moscarello M A, Harauz G. 2001. The effects of deimination of myelin basic protein on structures formed by its interaction with phosphoinositide-containing lipid monolayers. J Struct Biol 136(1):30-45.

Ishigami, A., Ohsawab, T., Asagab, H., Akiyama, K., Kuramotoa, M., Maruyamaa, N. 2002. Human peptidylarginine deiminase type II: molecular cloning, gene organization, and expression in human skin. Archives of Biochemistry and Biophysics 407(1): 25-31.

Lutgens L C, Blijlevens N M, Deutz N E, Donnelly J P, Lambin P, de Pauw B E. 2005. Monitoring myeloablative therapy-induced small bowel toxicity by serum citrulline concentration: a comparison with sugar permeability tests. Cancer 103(1): 191-1999.

Lutgens L C, Deutz N, Granzier-Peeters M, Beets-Tan R, De Ruysscher D, Gueulette J, Cleutjens J, Berger M, Wouters B, von Meyenfeldt M, Lambin, P. 2004. Plasma citrulline concentration: a surrogate end point for radiation-induced mucosal atrophy of the small bowel. A feasibility study in 23 patients. Int J Radiat Oncol Biol Phys. 60(1): 275-285.

Lutgens L C, Deutz N E, Gueulette J, Cleutjens J P, Berger M P, Wouters B G, von Meyenfeldt M F, Lambin P. 2003. Citrulline: a physiologic marker enabling quantitation and monitoring of epithelial radiation-induced small bowel damage. Int J Radiat Oncol Biol Phys. 57(4):1067-1074.

Lutgens L, Lambin P. 2007. Biomarkers for radiation-induced small bowel epithelial damage: an emerging role for plasma Citrulline. World J Gastroenterol. 13(22): 3033-3042.

Kanno T, Kawada A, Yamanouchi J, Yosida-Noro C, Yoshiki A, Shiraiwa M, Kusakabe M, Manabe M, Tezuka T, Takahara H. 2000. Human peptidylarginine deiminase type III: molecular cloning and nucleotide sequence of the cDNA, properties of the recombinant enzyme, and immunohistochemical localization in human skin. J Invest Dermatol 115(5): 813-823.

Nakashima K, Hagiwara T, Ishigami A, Nagata S, Asaga H, Kuramoto M, Senshu T, Yamada M. 1999. Molecular characterization of peptidylarginine deiminase in HL-60 cells induced by retinoic acid and 1alpha,25-dihydroxyvitamin D(3). J Biol Chem 274(39): 27786-27792.

Ossetrova N I, Farese A M, MacVittie T J, Manglapus G L, Blakely W F. 2007. The use of discriminant analysis for evaluation of early-response multiple biomarkers of radiation exposure using non-human primate 6-Gy whole-body radiation model, Radiation Measurements 42: 1158-1163.

Peters J H, Berridge B J Jr, Chao W R, Cummings J G, Lin S C. 1971. Amino acid patterns in the plasma of old and new world primates. Comparative biochemistry and physiology, 39(3): 639-647.

Peters J H, Smith C C. Amino acids and L-asparaginase activity in the plasma of owl monkeys (*Aotus trivirgatus*). 1972. Journal of medical primatology 1(5): 326-332.

Peters J H, Tanaka T. 1972. Amino Acids in the Plasma of Fasting Japanese Monkeys (*Macaca fuscata fuscata* and *M. f. yakui*). Primates 13(3): 271-276.

Rogers, G. E. 1962. Occurrence of citrulline in proteins. Nature 194: 1149-1151.

Rogers G, Winter B, McLaughlan C, Powell B, Nesci T. 1997. Peptidylarginine deiminase of the hair follicle: characterization, localization, and function in keratinizing tissues. J Invest Dermatol 108(5): 700-707.

Stegink L D, Reynolds W A, Pilkin R M, Cruikshank D P. 1981. Placental transfer of taurine in the rhesus monkey. The American Journal of Clinical Nutrition 34: 2685-2692.

Stone, H. B., Moulder, J. E., Coleman, C. N., Ang, K. K., Anscher, M. S., Barcellos-Hoff, M. H., Dynan, W. S., Fike, J. R., Grdina, D. J., Greenberger, J. S., Hauer-Jensen, M., Hill, R. P., Kolesnick, R. N., Macvittie, T. J., Marks, C., McBride, W. H., Metting, N., Pellmar, T., Purucker, M., Robbins, M. E., Schiestl, R. H., Seed, T. M., Tomaszewski, J. E., Travis, E. L., Wallner, P. E., Wolpert, M., Zaharevitz, D. 2004. Models for evaluating agents intended for the prophylaxis, mitigation and treatment of radiation injuries. Report of an NCI Workshop, Dec. 3-4, 2003. Radiation Research 162(6): 711-728.

Vanuxem P, Vanuxem D, Formaris E, Bernasconi P. 1986. The role of lactate and ammonium in fatigue. Gazette Medicale 7: 62-72.

Verleye M, Heulard I, Stephens J R, Levy R H, Gillardin J M. 1995. Effects of citrulline malate on bacterial lipopolysaccharide induced endotoxemia in rats. Arzneimittel-Forschung 45(6): 712-715.

Wood D D and Moscarello M A. 1989. The isolation, characterization, and lipid-aggregating properties of a citrulline containing myelin basic protein. J Biol Chem 264(9): 5121-5127.

The invention claimed is:

1. A method for treating radiation injury and exposure in a first mammal, comprising the steps of:
   obtaining one or more test samples from the first mammal;
   contacting the test samples with an antibody immunoreactive with a citrullinated protein to form an immunocomplex;
   detecting the immunocomplex with an enzyme-linked immunosorbent assay (ELISA);
   determining the degree of radiation injury and exposure to the first mammal, wherein a decrease in the quantity of the immunocomplex in the test samples, as compared to a control sample from at least one second mammal known to have a lower degree of radiation injury or exposure, indicates a higher degree of radiation injury and exposure to the first mammal; and
   providing medical treatment to the first mammal that is appropriate for the degree of radiation injury and exposure experienced by the first mammal.

2. The method of claim 1, wherein the first mammal is human.

3. The method of claim 1, wherein the one or more test samples is selected from the group consisting of blood, plasma, serum, skin, tissue, and urine.

4. The method of claim 1, wherein the radiation injury is small bowel damage.

5. The method of claim 4, wherein the small bowel damage leads to epithelial cell loss.

6. The method of claim 1, wherein the citrullinated protein is selected from the group consisting of trichohyalin, keratin, filaggrin, myelin basic protein (MBP), and histones.

7. The method of claim 1, further comprising measuring the level of at least one hematological parameter in the one or more test samples, wherein a decreased quantity of the immunocomplex in the test samples and decreased level of at least one hematological parameter in the test samples, as compared to a control sample from the at least one second mammal known to have a lower degree of radiation injury or exposure, indicates a higher degree of radiation injury and exposure to the first mammal.

8. The method of claim 7, wherein the at least one hematological parameter is peripheral cell counts.

9. The method of claim 8, wherein the peripheral cell counts comprise one or more of white blood cell levels, red blood cell levels, lymphocyte levels, and/or platelet levels.

* * * * *